United States Patent [19]

Ihida

[11] 4,248,997
[45] Feb. 3, 1981

[54] PROCESS FOR PRODUCING CURABLE ESTERIFIED ALKYD RESINS

[75] Inventor: Kazuyoshi Ihida, Tokyo, Japan

[73] Assignee: Toyo Ink Manufacturing Co., Ltd., Tokyo, Japan

[21] Appl. No.: 61,576

[22] Filed: Jul. 30, 1979

[51] Int. Cl.$^3$ .......................................... C08F 222/04
[52] U.S. Cl. ............................... 528/272; 204/159.19; 204/159.22; 528/273; 528/298; 525/168
[58] Field of Search ............................... 528/272, 298

[56] References Cited

U.S. PATENT DOCUMENTS

| 3,287,395 | 11/1966 | Chang .................................... 528/272 |
| 4,113,593 | 9/1978 | Barzynski et al. .............. 204/159.19 |

Primary Examiner—Edward M. Woodberry
Attorney, Agent, or Firm—Jordan and Hamburg

[57] ABSTRACT

A process for the production of a final curable resin comprising the steps of reacting a cyclopentadiene type compound with a compound having a double bond and hydroxyl group in the molecule to obtain a hydroxyl group-containing resin, reacting the thus obtained resinous polyol and at least one other polyol with a polybasic acid to obtain a hydroxyl group-containing alkyd resin and then esterifying the alkyd resin with an $\alpha,\beta$-unsaturated carboxylic acid thereby obtain the final curable resin. In one embodiment, this invention relates to said final curable resins and also to curable coating compositions containing same.

21 Claims, 3 Drawing Figures

PROCESS FOR PRODUCING CURABLE ESTERIFIED ALKYD RESINS

This invention relates to a process for producing a curable resin comprising esterifying a hydroxy group-containing alkyd resin, prepared from a resinous polyol, with an α,β-unsaturated carboxylic acid, to the curable resin and to a curable coating composition for use in the preparation of inks, paints or the like.

There have recently been required capability of quick drying and dispensability with solvents in the recent printing inks and paints, and, therefore, there have been increasingly utilized printing inks and paints which are curable by the action of activating rays such as ultraviolet rays and electronic beams.

Heretofore, known resins which are curable by the action of activating rays (hereinafter referred to as "curable resins" for brevity) include epoxyacrylate resins, acrylated fatty acid-modified alkyd resins and fatty acid-modified alkyd/polyisocyanate/acrylate resins.

However, these known curable resins have the following drawbacks.

Epoxyacrylate resins have excellent curability, however, they are highly viscous for their molecular weight due to the presence of hydroxy groups in the molecule whereby they are made unsatisfactory in handling or treatment when used for printing, coating or the like. In addition, when they are used in the preparation of inks, the resulting inks will greatly depend for their fluidity prior to being cured, their transfer property and the like upon temperatures whereby they are degraded in handling. Films or coatings prepared from these inks will produce great strains therein when cured, whereby they do not securely adhere to substrates. Further, said films or coatings are brittle and consequently poor in workability.

Acrylated fatty acid-modified alkyd resins will form unsatisfactorily hard films softened due to the plasticization of the acrylated resins with the alkyl group present in the fatty acid, and, because of this, the films are inferior in solvent resistance.

Fatty acid-modified alkyd/polyisocyanate/acrylate resins are highly viscous due to the urethane linkages in the molecule thereby to make it inconvenient to handle said acrylates. These resins require a relatively large amount of reactive solvents to be incorporated therein to lower their viscosity whereby they are disadvantageously degraded in curability.

In addition to the aforesaid curable resins, acrylated copolymers of cyclopentadiene or dicyclopentadiene with allyl alcohol are disclosed by Japanese Patent Application Laying-Open Gazette No. 124133/74. However, the curable resins so disclosed are disadvantageous in that they greatly depend on temperatures due to their low molecular weight and have unsatisfactory pigment dispersibility because of low polarity effects.

The present inventor made intensive studies in attempts to overcome said disadvantages and, as a result of his studies, he succeeded in preparing curable resins which have a wide distribution of molecular weight and are excellent in solubility, curability and film workability and he also succeeded in preparing curable coating compositions containing said resins, the compositions being useful in the preparation of inks, paints or the like.

An object of this invention is to provide a process for the production of a final curable resin comprising the steps of:

reacting (A) a five-membered cyclic compound having unsaturated conjugated double bonds and being represented by the following general formula

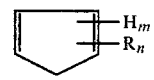

wherein R is an organic residue (such as an alkyl group) containing 1–3 carbon atoms, m and n are each an integer and the total of m and n is 6, and/or a Diels-Alder's reaction product of the five-membered cyclic compound, with (B) a compound having a polymerizable double bond and at least one hydroxyl group in the molecule, to obtain a hydroxyl group-containing resin (I), selectively hydrogenating the thus obtained resin (I) only at the double bonds to obtain a selectively hydrogenated resin (II) if desired, reacting a polycarboxylic acid with at least one member selected from the group consisting of the resins (I) and (II) as polyols and a polyol other than said resins to obtain a hydroxyl group-containing alkyd resin (III) and then esterifying the thus obtained hydroxyl group-containing alkyd resin (III) with an α,β-unsaturated carboxylic acid to obtain a final curable resin (IV).

Another object of this invention is to provide the final curable resin (IV) produced by the above process.

A still another object is to provide a curable coating composition comprising the final curable resin (IV), a photosensitive agent, a pigment, and a viscosity-adjusting momomer.

Unlike conventional curable resins, the curable resins of this invention will not decrease in solubility if they are produced with a high molecular weight nor will they decrease in curability if they contain plastic materials in increased amounts. The reason for this is that a resinous polyol having a high molecular weight and satisfactory solubility is used as a part of polyols used in the production of an alkyd resin, thereby resulting in producing a final curable resin, such as an acrylated alkyd resin, of this invention having satisfactory solubility and a high molecular weight.

Therefore, curable coating compositions for printing inks, paints or the like, in which the final curable resin of this invention is used as the vehicle material, are excellent in curability, pigment dispersibility, workability and adhesiveness, have low dependency on temperatures and may be conveniently handled.

This invention will be further detailed hereinbelow.

In the preparation of the resin (I), component (A) and component (B) are used.

The component (A) is at least one member selected from the group consisting of cyclopentadiene, dicyclopentadiene, tricyclopentadiene, tetracyclopentadiene and the like as well as their substituted compounds, preferably their $C_1$–$C_3$ lower alkyl substituted compounds (such as methylcyclopentadiene), and the like.

The component (B) is at least one member selected from the group consisting of (meth)allyl alcohol, 2-hydroxyethyl (meth)acrylate, 1,4-butenediol, 1,3-butenediol, 2-hydroxypropyl (meth)acrylate and the like. The terms "(meth)allyl" and "(meth)acrylate" are intended to mean "allyl and methallyl" and "acrylate and methacrylate", respectively.

The components (A) and (B) may be reacted or polymerized together in molar ratios of from 30/70 to 95/5, preferably from 40/60 to 80/20. The polymerizing reaction may be effected at 150°–350° C. in the presence or absence of a radical catalyst, using a solvent if desired, at a superatmospheric pressure for 3–10 hours. After the end of the polymerizing reaction, the reaction mixture is freed of the low molecular weight compounds produced and the unreacted components thereby to obtain the resin (I) having a melting point of 60°–150° C. and consisting of a mixture of compounds having the following respective structures (a), (b), (c) and (d).

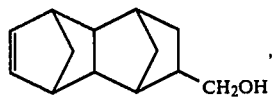
(a)

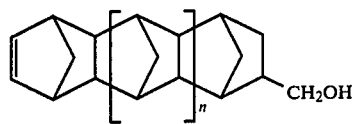
(b)

wherein n is an integer of 1–3,

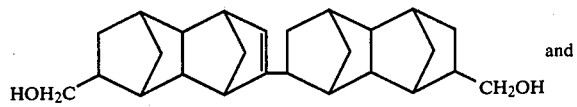
and
(c)

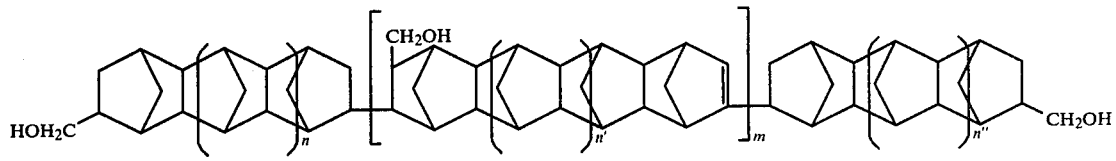
(d)

wherein n is an integer of 1–3, n' an integer of 1–3, n" an integer of 1–3 and m an integer of 1–5.

Said mixture contains the compound of structure (c) in an amount by weight of at least 80% thereof. Thus, the mixture may be expressed in the term "resinous polyol" in this invention. In the reaction between the components (A) and (B), cyclopentadiene and dicyclopentadiene are mainly used as the component (A) and allyl alcohol mainly used as the component (B) in many cases.

The resin (II) is prepared by selectively hydrogenating the double bonds of the resin (I) without decreasing the amount of the hydroxyl groups in the presence of a hydrogenation catalyst such as platinum, palladium, nickel or copper-chromium and, if desired, in the presence of a solvent, at a temperature from ambient to 250° C. and a pressure of from atmospheric to 100 Kg/cm². In this case, the degree of hydrogenation is not particularly limited but is such that at least 40%, preferably at least 80% of the inter-carbon double bonds in the resin (I) is hydrogenated.

The resin (II) so obtained by the hydrogenation of the resin (I) is less colored yellow, less odorous and more excellent than the resin (I) (the resins (I) and (II) being hereinafter generally referred to as "DCPD polyol").

In this invention, the DCPD polyol is used as a part of polyols used in the preparation of the hydroxyl group-containing alkyd resin (III).

The polyols which may be used in this invention include, in addition to the DCPD polyol, aliphatic polyols such as glycerine, trimethylolpropane, pentaerithritol, dipentaerithritol and tripentaerithritol; glycols such as ethylene glycol, diethylene glycol, propylene glycol, dipropylene glycol, tripropylene glycol and neopentyl glycol; and cyclic polyols such as trimethylol isocyanurate, trimethylolmelamine and hexamethylolmelamine. These polyols may be used alone or jointly.

The polybasic acids which may be used in the preparation of the hydroxyl group-containing alkyd resins, include adipic acid, succinic acid, fumaric acid, maleic acid, maleic anhydride, isophthalic acid, phthalic anhydride, terephthalic acid, trimellitic acid, trimellitic anhydride, tetrahydrophthalic anhydride and hexahydrophthalic anhydride. These acids and acid anhydrides may be used alone or jointly.

In the preparation of the hydroxyl group-containing alkyd resins (III), there may be used, together with the aforesaid polybasic acids, linseed oil, rice bran oil, caster oil, dehydrated castor oil, palm oil, tung oil and the fatty acids thereof as well as saturated fatty acids such as caproic acid, caprylic acid, capric acid, lauric acid, myristic acid, palmitic acid, stearic acid and arachic acid, unsaturated fatty acids such as oleic acid, linolic acid, linolenic acid, eleostearic acid and ricinoleic acid, and rosin compounds such as rosin, hydrogenated rosin, dismutated rosin and polymerized rosin.

These compounds may be used alone or jointly in amounts of not more than 50 parts by weight per 100 parts by weight of the polyols and polybasic acid in total. The use of more than 50 parts of said compounds will result in the production of a hydroxyl group-containing alkyd resin having a decreased molecular weight, and cured films prepared from the resulting resin are plasticized ones having inferior solvent resistance.

If further necessary in the preparation of the alkyd resin (III), there may additionally be used monohydric alcohols such as methanol, ethanol, propanol, butanol, hexanol, octanol, benzyl alcohol, cyclohexanol, ethylene glycol monoalkyl ether and oxoalcohol.

The hydroxyl group-containing alkyd resins (III) according to this invention are synthesized by charging 20–80 parts by weight of the DCPD polyol, 5–50 parts by weight of at least one polyol other than the DCPD polyol, 10–50 parts by weight of a polybasic acid and, if desired, up to 50 parts by weight, per 100 parts by weight of the total of all the polyols and the polybasic acid, of at least one optional compound such as the aforesaid aliphatic oil, fatty acid, rosin or a monohydric alcohol, into a four-necked flask provided with a stirrer and a condenser to form a mixture which is reacted at 150°–280° C. while removing water produced by the condensation from the reaction system. The reaction is continued until the resulting hydroxyl group-containing alkyd resin (III) has an acid value of not more than 20, preferably not more than 10.

In the aforementioned synthesis, it is necessary to use 20–80 parts by weight of the DCPD polyol and, the use of less than 20 parts by weight thereof will result in raising the melting point and lowering the mineral oil solubility of an alkyd resin to be synthesized since the portion of polyesters to be obtained by reacting the polyol other than the DCPD polyol with the polybasic acid is increased. If a final curable resin obtained using such an alkyd resin is employed in the preparation of printing inks or paints, the resulting inks or paints will degrade in fluidity and provide prints or coatings having unsatisfactory properties such as inferior surface gloss.

On the other hand, the use of more than 80 parts by weight of the DCPD polyol will result in decreasing crosslinking reactions and therefore producing an alkyd resin having a decreased molecular weight. Printing inks or the like prepared using the thus produced alkyd resin will be inferior in printability, curability and drying property.

In cases where it is desired to avoid the production of polyesters as a by-product by reacting a part of the polybasic acid with the polyol other than the DCPD polyol, it is preferable that the DCPD polyol be esterified with the polybasic acid, in the presence of an aliphatic oil, fatty acid, rosin and a monohydric alcohol as required, prior to adding the polyol other than the DCPD polyol to the reaction system.

The amount of hydroxyl groups contained in the hydroxyl group-containing alkyd resin (III) is 120–1260, preferably 150–300, expressed in terms of OH equivalent.

The hydroxyl group-containing alkyd resin (III) is esterified with an $\alpha,\beta$-unsaturated carboxylic acid to obtain a final curable resin (IV). The $\alpha,\beta$-unsaturated carboxylic acids include acrylic, methacrylic, crotonic and sorbic acids, and they may be used alone or in combination. Among these carboxylic acids, acrylic acid and methacrylic acid are preferred from the view-point of the solubility and curability of a final curable resin to be obtained. In addition, it is preferable to use the $\alpha,\beta$-unsaturated carboxylic acid in an amount of 5–50, preferably 10–35, parts by weight per 95–50 parts by weight of the hydroxyl group-containing alkyd resin (III) in order to obtain a final curable resin (IV) having satisfactory curability, molecular weight distribution and solubility.

The reaction of the hydroxyl group-containing alkyd resin (III) with the $\alpha,\beta$-unsaturated carboxylic acid is achieved by introducing 95–50 parts by weight of the alkyd resin (III), 10 parts by weight of a solvent for reflux such as cyclohexane, and 0.1 part by weight of a thermal polymerization inhibitor into a four-necked flask fitted with a stirrer and a reflux condenser to form a mixture, adding 5–50 parts by weight of the $\alpha,\beta$-unsaturated carboxylic acid to the thus formed mixture at 80° C., reacting the acid with the mixture at 100°–120° C. while removing water produced by the condensation reaction from the reaction system until the acid value of the resulting reaction mixture reaches 30 or less, preferably 20 or less, and then removing the reflux solvents such as cyclohexane to obtain a final curable resin (IV) of this invention.

The final curable resins (IV) are those which eliminate the various conventional drawbacks and they are suitable as the component resin of curable coating compositions for printing inks, paints or the like accordingly.

Ultraviolet light curable printing inks in which the final curable resin (IV) of this invention is used, may preferably comprise, by weight, 15–65 parts of the final curable resin (IV), 1–25 parts of a photosensitizer, 5–50 parts of a pigment, 5–50 parts of a viscosity-adjusting monomer and, if desired, other suitable additives.

Ultraviolet light curable paints in which the resin (IV) is used, may preferably comprise, by weight, 5–20 parts of the resin (IV), 1–25 parts of a photosensitizer, 0–60 parts of a pigment, 15–60 parts of a viscosity-adjusting monomer and, if desired, other suitable additives.

The photosensitizers which may be used in the preparation of the ultraviolet light curable coating compositions, include benzoin, benzoin methyl ether, benzoin ethyl ether, benzoin propyl ether, benzoin butyl ether, benzophenone, benzil, xanthone, thioxanthone, methyl benzoylbenzoate, ethyl benzoylbenzoate, acetophenone, 4-dimethylaminoacetophenone, methyl-p-dimethylaminobenzoate, ethyl m-dimethylaminobenzoate, amyl p-dimethylaminobenzoate, amyl o-dimethylaminobenzoate and 4,4'-bisdiethylaminobenzophenone. These photosensitizers may be used alone or in combination.

The viscosity-adjusting monomers which may be used in this invention, include trimethylolpropane triacrylate, trimethylolpropane trimethacrylate, pentaerithritol triacrylate, pentaerithritol trimethacrylate, dipentaerithritol polyacrylate, dipentaerithritol polymethacrylate, triallyl isocyanurate, triallyl citrate, polyethylene glycol diacrylate, ethylene glycol dimethacrylate, polypropylene glycol diacrylate, phenylglycidyl acrylate and phenylene diglycol diacrylate. These viscosity-adjusting monomers may be used alone or in combination.

Furthermore, the pigments used herein include organic pigments such as azo pigments (Hansa Yellow, Benzidine Yellow, Lake Red C, carmine 6B, Permanent Red 2B and the like), phthalocyanine pigments (phthalocyanine blue, phthalocyanine green and the like), quinacridone pigments, isoindolinone pigments and quinophthalone pigments and also include inorganic pigments such as titanium dioxide, carbon black, rouge, zinc oxide and calcium carbonate.

In cases where the final curable resin (IV) is attempted to be cured by heating, an organic peroxide may be used alone or in combination with cobalt naphthenate, manganese naphthenate or the like.

This invention will be better understood by reference to Examples and Comparative Examples wherein all parts are by weight unless otherwise specified.

EXAMPLE 1

Six hundred and sixty (660) grams of 96% pure dicyclopentadiene, 300 g of allyl alcohol and 500 g of commercially available xylenes were introduced into an autoclave provided with a stirrer to form a mixture which was reacted at 260° C. for 5 hours to obtain the reaction mixture. After the end of the reaction the autoclave was cooled and the reaction mixture so obtained was heated to 200° C. at a reduced pressure of 1–0.3 atm. for 3 hours to distil off the unreacted monomer, low polymers and the xylene thereby obtaining 750 g of a resin (I)-1. One hundred (100) grams of the thus obtained resin (I)-1 were dissolved in 75 g of commercially available xylenes, incorporated with 1 g of palladium carbon containing palladium in a 5% concentration (5% Pd-C Standard grade produced by Japan Engerhart Co.), subjected to hydrogenation reaction at a temperature of 150° C. and a hydrogen pressure of 30 Kg/cm$^2$ for about one hour and then removing the solvent thereby to obtain a hydrogenated resin (II)-1. The properties of the resins (I)-1 and (II)-1 are as follows:

| | Softening point | Bromine number | Content of hydroxyl group (g equivalent/100g) | Color (Gardner) |
|---|---|---|---|---|
| Resin (I)-1 | 90° C. | 74 | 0.37 | 10 |
| Resin (II)-1 | 86° C. | 16 | 0.37 | 3 |

Then, 45 parts of the resin (I)-1, 29 parts of phthalic anhydride and 26 parts of trimethylolpropane were charged into a four-necked flask provided with a stirrer and a reflux condenser to form a mixture which was reacted at 240° C. under a nitrogen (N$_2$) atmosphere for 7.5 hours thereby to obtain a hydroxyl group-containing alkyd resin (III)-1 having an acid value of 7.8. Eighty (80) parts of the thus obtained alkyd resin (III)-1, 20 parts of acrylic acid, 1 part of p-toluenesulfonic acid and 0.1 part of hydroquinone were charged into a four-necked flask provided with a stirrer and a reflux condenser to form a mixture. The mixture so formed was reacted at 80°–120° C. under reflux of a cyclohexane/methyl isobutyl ketone (2:1) mixture for 15 hours until the reaction mixture had an acid value of 20.5. This reaction mixture was heated to 115° C. to distil off the reflux solvent (cyclohexane/methyl isobutyl ketone (MIBK)) thereby obtaining a final curable resin (IV)-1 having an acid value of 18.3.

EXAMPLE 2

Forty-five (45) parts of the resin (II)-1 as obtained in Example 1, and 29 parts of Rikacid TH (tetrahydrophthalic anhydride produced by Shin Nippon Rika Co., Ltd.) were charged into a four-necked flask provided with a stirrer and a reflux condenser to form a mixture which was reacted at 150° C. for 1.5 hours under reflux of commercially available xylene while blowing gaseous N$_2$ into the reaction system to obtain a reaction mixture. The reaction mixture so obtained was incorporated with 26 parts of trimethylolpropane and then reacted together at 200° C. for 5 hours thereby to obtain a hydroxyl group-containing alkyd resin (III)-2.

Then, 80 parts of the thus obtained alkyd resin (III)-2, 1 part of p-toluenesulfonic acid, 0.1 part of hydroquinone and 15 parts of a cyclohexane/MIBK (2:1) mixed solvent were mixed together, heated to 80° C., incorporated with 20 parts of acrylic acid, reacted at 100° C. for 16 hours while blowing air into the reaction system until the resulting reaction mixture had an acid value of 18.3 and then removing the solvent from the reaction mixture at 115° C. for 3 hours thereby to obtain a final curable resin (IV)-2 having an acid value of 16.4.

The infra-red absorption spectrum for the final curable resin (IV)-2 is indicated in FIG. 1 in which the peaks based on the ester groups of said resin are appreciated respectively at wave numbers of 1730 cm$^{-1}$ and 1190 cm$^{-1}$. Further, the distribution of molecular weight of the resin (IV)-2 is indicated in FIG. 2. This resin has a molecular weight (Mw) of 3765 and a number average molecular weight (Mn) of 638 with the ratio of Mw/Mn being 5.9.

Figure 1:
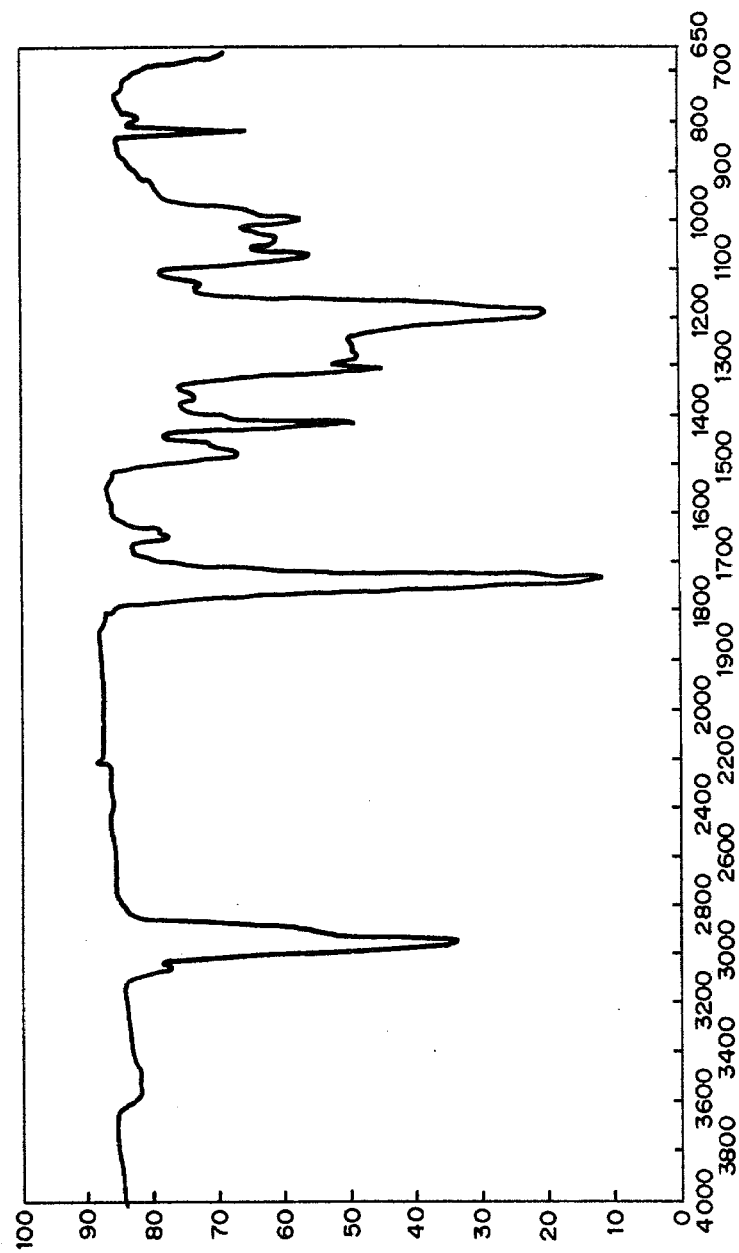
FIG. 1 is an infra-red chart for the final curable resin (IV)-2.

In this Figure, Fd, Fh and Fp indicate dispersion effect, hydrogen bond effect and polarity effect, respectively, and what is indicated by each of the numerals is as follows:

1: O sol-H (n-paraffin produced by Nippon Oil Co., Ltd.), 2: cyclohexane, 3: carbon tetrachloride, 4: xylene, 5: benzene, 6: trichloroethylene, 7: dichlorobenzene, 9: nitrobenzene, 10: propylene glycol, 11: ethyl acetate, 12: Cellosolve acetate, 13: 1-chlorobutane, 14: D.M.F., 15: ethanolamine, 16: diethylene glycol, 17: water, 18: ethylene glycol, 19: n-butanol, 20: isooctyl alcohol; 21, ethyl Cellosolve, 22: ethyl alcohol, 23: tetrahydrofuran, 24: morpholine, 25: pyridine; 26, methyl carbitol, 27: n-butyl acetate, 28: cyclohexanol, 29: D.E.P., 30: D.M.P., 31: D.O.P., 32: tributyl monoacetyl citrate, 33: D.B.M., 34: D.O.A., 35: 2-ethyl butanol, 36: dipropylene glycol, 37: butyronitrile, 38: cyclohexyl chloride, 39: diacetone alcohol.

EXAMPLE 3

Eighty-two (82) parts of the hydroxyl group-containing alkyd resin (III)-2 as obtained in Example 2, 1 part of p-toluenesulfonic acid, 0.1 part of hydroquinone and 15 parts of a cyclohexane/MIBK (2:1) mixed solvent were mixed together to form a mixture which was heated to 80° C., incorporated with 18 parts of methacrylic acid, reacted at 100° C. for 14 hours while blowing air into the reaction system until the resulting reaction mixture had an acid value of 19.7 and then heated to 115° C. to distil off the solvent for 3 hours thereby obtaining a final curable resin (IV)-3 having an acid value of 17.8.

EXAMPLE 4

Forty-three (43) parts of the resin (II)-1 as obtained in Example 1, 10 parts of rosin, 23.5 parts of adipic acid and 24 parts of pentaerithritol were reacted together in the same manner as in Example 1 to obtain a hydroxyl group-containing alkyd resin (III)-4 having an acid value of 10.6.

Then, 75 parts of the thus obtained alkyd resin (III)-4 and 25 parts of acrylic acid were reacted with each other in the same manner as in Example 1 to obtain a final curable resin (IV)-4 having an acid value of 16.9.

EXAMPLE 5

Twenty-seven (27) parts of the resin (II)-1 as obtained in Example 1, 11.2 parts of 2-ethylbutanol, 32.5 parts of Rikacid HH (hexahydrophthalic anhydride produced by Shin Nippon Rika Co.) and 29.2 parts of trimethylolpropane were reacted together in the same manner as in Example 2 to obtain a hydroxyl group-containing alkyd resin (III)-5.

Then, 78 parts of the thus obtained alkyd resin (III)-5 and 22 parts of acrylic acid were reacted together in the same manner as in Example 1 or 2 to obtain a final curable resin (IV)-5 having an acid value of 16.3.

EXAMPLE 6

A printing ink was prepared using each of the final curable resins (IV)-1 to (IV)-5 as obtained in Examples 1–5.

Sixty-five (65) parts of each of said final curable resins were incorporated with 35 parts of phenylene diglycol diacrylate to produce an ink vehicle. Then, 43 parts of each of the thus produced ink vehicles, 40 parts of CR 80 (titanium dioxide produced by Ishihara Sangyo K. K.), 10 parts of benzil, 0.2 parts of 4-dimethylaminoacetophenone and 7 parts of phenylene diglycol diacrylate were mixed together by the use of a three-roll mill to obtain an ink. Thus, there were obtained inks 1 to 5 corresponding respectively to the final curable resins (IV)-1 to (IV)-5.

COMPARATIVE EXAMPLE 1

Seventy-eight (78) parts of the resin (II)-1 as obtained in Example 1, 1.0 part of p-toluenesulfonic acid, 0.1 part of hydroquinone and 15 parts of a cyclohexane/MIBK (2:1) mixed solvent were charged into a four-necked flask provided with a stirrer and a reflux condenser to form a mixture. The mixture so formed was heated to 80° C., incorporated with 22 parts of acrylic acid, reacted together at 100° C. for 7.5 hours until the resulting reaction mixture had an acid value of 18.0 and then heated to 115° C. for 3 hours to distil off the cyclohexane/MIBK (2:1) mixed solvent thereby obtaining a comparative final curable resin (V)-6 having an acid value of 15.4.

COMPARATIVE EXAMPLE 2

Seventy-five (75) parts of Epikote 828 (epoxy resin produced by Shell Petrochemical Incorporation), 0.1 part of hydroquinone and 0.2 parts of ethylenediamine were charged into a four-necked flask provided with a stirrer and a reflux condenser to form a mixture. The mixture so formed was heated to 80° C., incorporated with 25 parts of acrylic acid and then reacted together at 100° C. for 18 hours to obtain a comparative final curable resin (V)-7 having an acid value of 3. The procedure of Example 6 was followed except that each of the curable resins (V)-6 and (V)-7 was used, to obtain printing inks 6 to 7 corresponding respectively to said resins (V)-6 and (V)-7.

The final curable resins and the inks as obtained in the Examples and Comparative Examples had the properties and evaluations as indicated in Tables 1 and 2.

TABLE 1

| Property | Final curable resin | | | | | | |
|---|---|---|---|---|---|---|---|
| | (IV)-1 | (IV)-2 | (IV)-3 | (IV)-4 | (IV)-5 | (IV)-6 | (IV)-7 |
| Acid value | 18.3 | 16.4 | 17.8 | 16.9 | 16.3 | 15.4 | 3 |
| Compatibility with alkylbenzene | O | O | O | O | O | Δ | X |
| Compatability with phenylene diglycol diacrylate | O | O | O | O | O | Δ | O |
| Viscosity (Gardner*) | J⁺ | J | I | K⁻ | I⁻ | E | D⁺ |

*Viscosity obtained by measuring at 25° C. a 50% solution of each of the resins in diethylene glycol monobutyl ether for viscosity.

TABLE 2

| Ink | Evaluation of ink | | | | |
|---|---|---|---|---|---|
| | Gloss | Drying property[1] | Adhesiveness[2] | Workability | Printability[3] |
| Ink 1 | O | 70 m/min | 80/100 | O | Satisfactory |
| Ink 2 | O | 80 m/min | 100/100 | O | " |
| Ink 3 | O | 40 m/min | 100/100 | O | " |
| Ink 4 | O | 75 m/min | 100/100 | O | " |
| Ink 5 | O | 70 m/min | 100/100 | O | " |
| Ink 6 | Δ | 40 m/min | 80/100 | O | Ink transferability found unsatisfactory at the time of starting printing. |
| Ink 7 | Δ | 80 m/min | 20/100 | X | Tinting occurred. |

(1) The ink printed on the substrate was measured for its drying property expressed in terms of conveyor speed (m/min) by passing a conveyor on which the ink printed substrate was placed, 10 cm below a high pressure mercury lamp having an input power of 80 W/cm and a capacity of 5.6 KW input (manufactured by Toshiba Electrical Co., Ltd.) at such a conveyor speed that the ink could be cured by its passage below the lamp.

(2) The ink printed on an alkyd resin type size coated tin plate was subjected to a cross-cut test for its adhesiveness.

(3) The ink was used in offset printing by the use of a Heidelberg KORD offset press to make a test for printability.

Figure 2:
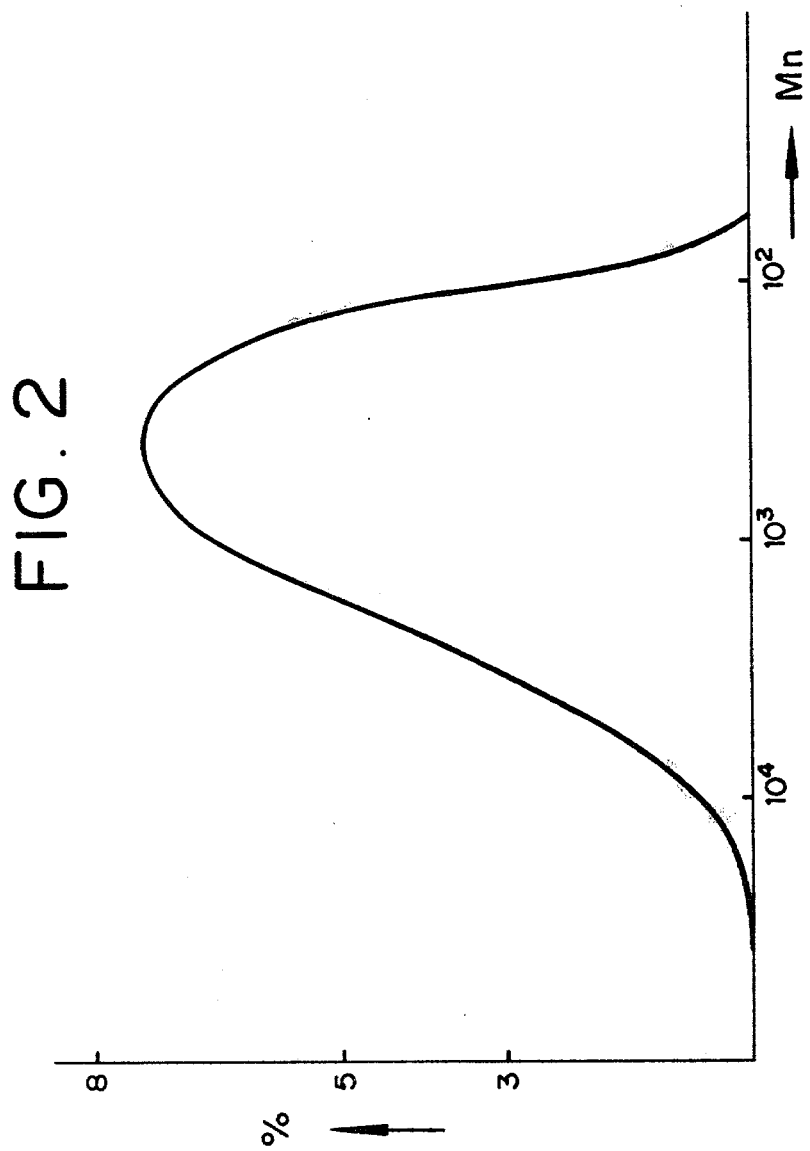
FIG. 2 is a graph showing the distribution of molecular weight of the final curable resin (IV)-2.
Figure 3:
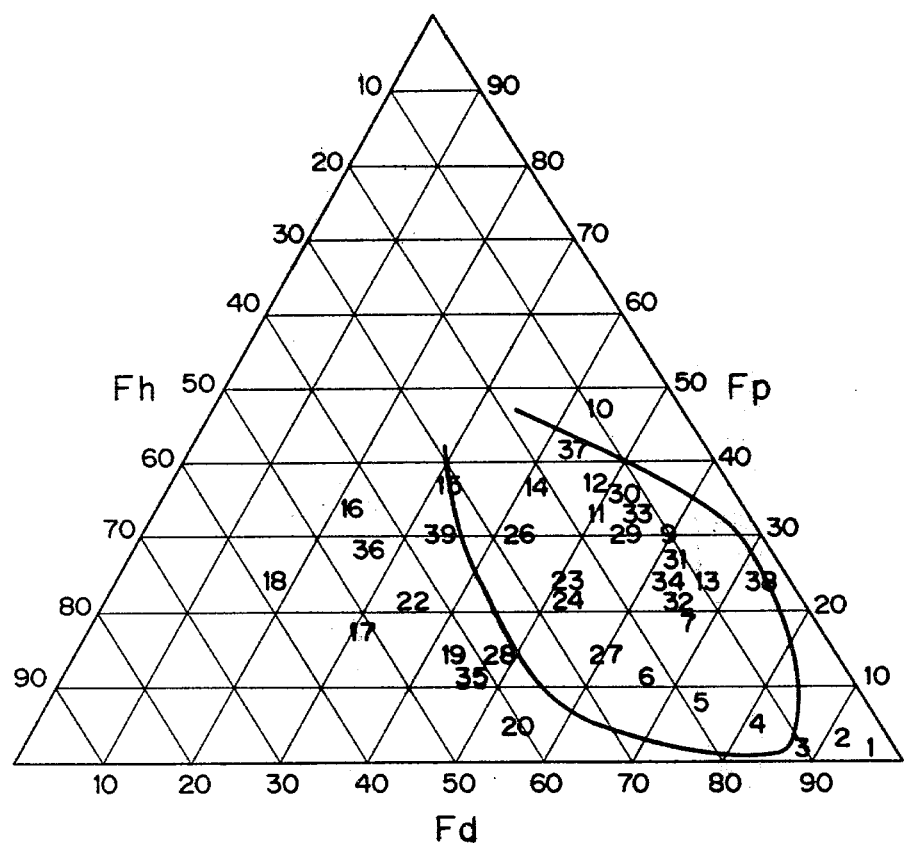
FIG. 3 is a graph showing a range of at least 90% tolerance for the final curable resin (IV)-2. The term "tolerance 90%" is intended to mean a point at which a resin diluted with a solvent in a ratio by weight of 10:90 is made white-turbid at 25° C.

It is seen from Table 1 that the final curable resins of this invention are satisfactory in compatibility with alkylbenzenes or phenylene diglycol diacrylate. FIG. 3 shows that the final curable resins of this invention have a wide range of solvent solubility and satisfactory dispersibility and are approximate to the solubility of rosin-modified phenol resins. In addition, FIG. 2 shows that the final resins of this invention have a considerably wide distribution of molecular weight.

As is also seen from Table 2, inks in which the composition of this invention is used will exhibit very excellent gloss, drying property, adhesiveness, workability, printability and the like as compared with those in which a conventional known resin is used.

What is claimed is:

1. A process for the production of a final curable resin comprising the steps of:

reacting (A) at least one compound selected from the group consisting of a five-membered cyclic compound and a Diels-Alder's reaction product thereof, the five-membered cyclic compound having unsaturated conjugated double bonds and being represented by the following general formula

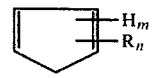

wherein R is an organic residue containing 1–3 carbon atoms, m and n are each an integer and the total of m and n is 6, with (B) at least one compound having a polymerizable double bond and a hydroxyl group in the molecule, to obtain a hydroxyl group-containing resin (I), reacting together (1) at least one resin as a polyol selected from the group consisting of the thus obtained resin (I) and a hydrogenated resin (II) obtained by the selective hydrogenation of only the double bonds of the resin (I), (2) a polyol other than said resins (I) and (II), and (3) a polybasic acid to obtain a hydroxyl group-containing alkyd resin (III), and then esterifying the thus obtained hydroxyl group-containing alkyd resin (III) with at least one α,β-unsaturated carboxylic acid to obtain the final curable resin (IV).

2. A process according to claim 1, wherein the at least one resin (1) as a polyol selected from the group consisting of the resins (I) and (II) is used in amounts by weight of 20-80% of the total of the at least one resin (1) and the other polyol (2).

3. A process according to claim 1 or 2, wherein the compound (A) for the resin (I) is cyclopentadiene, dicyclopentadiene, tricyclopentadiene, tetracyclopentadiene or a lower alkyl-substituted compound thereof.

4. A process according to claim 1 or 2, wherein the compound (B) for the resin (I) is (meth)allyl alcohol, 2-hydroxyethyl (meth)acrylate, 1,4-butenediol, 1,3-butenediol or 2-hydroxypropyl (meth)acrylate.

5. A process according to claim 3, wherein the compound (B) for the resin (I) is (meth)allyl alcohol, 2-hydroxyethyl (meth)acrylate, 1,4-butenediol, 1,3-butanediol or 2-hydroxypropyl (meth)acrylate.

6. A process according to claim 1 or 2, wherein the resin (I) is a mixture of four compounds (a) to (d) respectively having the following structural formulae:

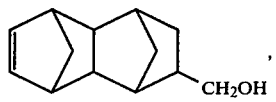
(a)

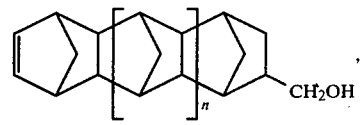
(b)

wherein n is an integer of 1 to 3,

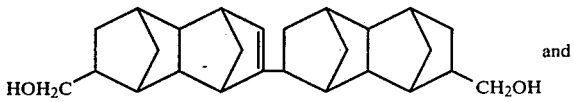
and

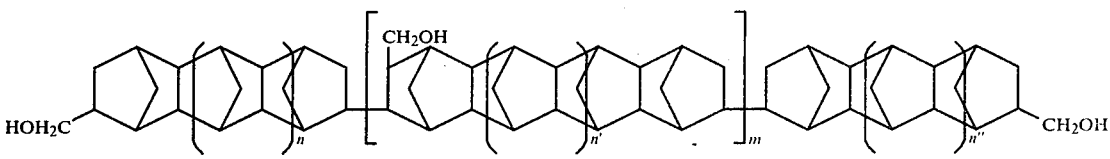
(d)

wherein n is an integer of 1 to 3, n' an integer of 1 to 3, n'' an integer of 1 to 3 and m an integer of 1 to 5.

7. A process according to claim 1 or 2, wherein the α,β-unsaturated carboxylic acid is acrylic acid, methacrylic acid, crotonic acid or sorbic acid.

8. A process according to claim 3, wherein the α,β-unsaturated carboxylic acid is acrylic acid, methacrylic acid, crotonic acid or sorbic acid.

9. A process according to claim 4, wherein the α,β-unsaturated carboxylic acid is acrylic acid, methacrylic acid, crotonic acid or sorbic acid.

10. A process according to claim 5, wherein the α,β-unsaturated carboxylic acid is acrylic acid, methacrylic acid, crotonic acid or sorbic acid.

11. A process according to claim 6, wherein the α,β-unsaturated carboxylic acid is acrylic acid, methacrylic acid, crotonic acid or sorbic acid.

12. A final curable resin (IV) obtained by the process of claim 1 or 2.

13. A final curable resin (IV) obtained by the process of claim 3.

14. A final curable resin (IV) obtained by the process of claim 4.

15. A final curable resin (IV) obtained by the process of claim 5.

16. A final curable resin (IV) obtained by the process of claim 6.

17. A curable coating composition comprising the final curable resin (IV), at least one photosensitizer, at least one pigment and at least one viscosity-adjusting monomer.

18. A curable coating composition according to claim 17, comprising, by weight, 15-65 parts of the final curable resin (IV), 1-25 parts of the photosensitizer, 5-50 parts of the pigment and 5-50 parts of the viscosity-adjusting monomer, the composition being useful for producing ultraviolet light curable printing inks.

19. A curable coating composition according to claim 17, comprising, by weight, 5-20 parts of the final curable resin (IV), 1-25 parts of the photosensitizer, 0-60 parts of the pigment and 15-60 parts of the viscosity-adjusting monomer, the composition being useful for producing ultraviolet light curable paints.

20. A process for the production of a final curable resin comprising the steps of:

reacting (A) at least one compound selected from the group consisting of a five-membered cyclic compound and a Diels-Alder's reaction production thereof, the five-membered cyclic compound having unsaturated conjugated double bends and being represented by the following general formula

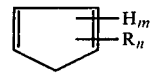
(c)

wherein R is an organic residue containing 1-3 carbon atoms, m and n are each an integer and the total of m and n is 6, with (B) at least one compound having a polymerizable double bond and a hydroxyl group in the molecule, to obtain a hydroxyl group-containing resin (I), reacting together (1) a resin as a polyol which is hydrogenated resin (II) obtained by the selective hydrogenation of only the double bonds of the resin (I), (2) a polyol other than said resin (II), and (3) a saturated polybasic acid to obtain a hydroxyl group-containing alkyd resin (III), and then esterifying the thus obtained hydroxyl group-containing alkyd resin (III) with at least one α,β-unsaturated carboxylic acid to obtain the final curable resin (IV).

21. A final curable resin (IV) obtained by the process of claim 20.

* * * * *